(12) United States Patent
Brossart et al.

(10) Patent No.: US 7,528,224 B1
(45) Date of Patent: May 5, 2009

(54) PEPTIDE FOR TRIGGERING AN IMMUNE REACTION AGAINST TUMOR CELLS

(75) Inventors: Peter Brossart, Reutlingen (DE); Stefan Stevanovic, Tubingen (DE); Wolfram Brugger, Kusterdingen (DE); Lothar Kanz, Tubingen (DE); Hans Georg Rammensee, Tubingen-Unterjessingen (DE)

(73) Assignee: Immatics Biotechnologies GmbH, Tubingen (DE)

( * ) Notice: Subject to any disclaimer, the term of this patent is extended or adjusted under 35 U.S.C. 154(b) by 204 days.

(21) Appl. No.: 11/414,897

(22) Filed: May 1, 2006

Related U.S. Application Data

(62) Division of application No. 10/019,513, filed as application No. PCT/EP00/02699 on Mar. 28, 2000, now Pat. No. 7,087,712.

(30) Foreign Application Priority Data

Apr. 16, 1999 (DE) ................................ 199 17 195

(51) Int. Cl.
*A61K 38/00* (2006.01)
*A61K 38/08* (2006.01)
(52) U.S. Cl. ............................ 530/300; 530/328; 514/2
(58) Field of Classification Search ........................ None
See application file for complete search history.

(56) References Cited

FOREIGN PATENT DOCUMENTS

| DE | 195 16 673 A1 | 10/1996 |
|---|---|---|
| EP | 0 823 438 A2 | 2/1998 |
| WO | WO 92/07000 | 4/1992 |
| WO | WO 96/03502 | 2/1996 |
| WO | WO 97/11715 | 4/1997 |
| WO | WO 98/37095 | 8/1998 |
| WO | WO 98/50527 | 11/1998 |
| WO | WO 00/06723 | 2/2000 |

OTHER PUBLICATIONS

Wiecrecky et al. (Cancer Research, Jun. 1, 2006, 66: 5910-5918).*
George et al. (2005, Trends in Immunology 26(12):653-659).*
Burgess et al (J of Cell Bio. 111:2129-2138, 1990).*
Coleman et al. (Research in Immunology, 1994; 145(1): 33-36).*
Abaza et al. (Journal of Protein Chemistry, vol. 11, No. 5, 1992, pp. 433-444).*
Lee et al (J. Immunol., 1999, 163:6292-6300).*
Chaux et al, (Int J Cancer, 1998, 77: 538-542).*
Kirkin et al (1998, APMIS, 106 : 665-679.*
Sherman et al. (Critical Reviews in Immunol, 1998, 18:47-54).*
Smith (Clin Immunol, 1994, 41(4): 841-849).*
Apostolopoulos et al. (J. Immunol., Dec. 1, 1997, 159:5211-5218).*
Brossart, et al. "The Epithelial Tumor Antigen MUC1 is Expressed in Hematological Malignancies and is Recognized by MUC1-Specific Cytotoxic T-Lymphocytes," *Cancer Research*, vol. 61, pp. 6846-6850, Sep. 15, 2001.
Brossart, et al. "Identification of HLA-A2-restricted T-Cell Epitopes Derived from the MUC1 Tumor Antigen for Broadly Applicable Vaccine Therapies," *Blood*, vol. 93, No. 12, pp. 4309-4317, Jun. 15, 1999.
European Search Report completed on Oct. 4, 2004 and issued to a related foreign application, EP 04013790.
Paul, *Fundamental Immunology*, (text), 1993, p. 1163.
Semino, et al., *J. Biol. Reg and Homeostatic Agents*, 1993. 7:99-105.
Algarra, et al., *Int. J. Clin. Lab. Res.*, 1997, 27:96-102.
Body, et al. *Anticancer Res.*, 2000, 20:2665-2676.
Lee, et al. *J. Immunol.*, 1999, 163:6292-6300.
Kirken, et al. 1998, APMIS, 106:665-679.
Chaux, et al. *Int. J. Cancer*, 1998, 7:538-542.
Sherman, et al. *Crit. Rev. Immunol*, 1998, 18:47-54.
Smith, *Clin. Immunol.* 1994, 41:841-849.
Boon *Adv Can Res*, 1992, 58:177-210.

\* cited by examiner

*Primary Examiner*—Karen A Canella
*Assistant Examiner*—Peter J Reddig
(74) *Attorney, Agent, or Firm*—Baker, Donelson, Bearman, Caldwell & Berkowitz, PC

(57) ABSTRACT

The invention relates to a peptide for triggering an immune response to tumor cells. Said peptide has an optionally modified fragment of the protein that is encoded by the gene MUC-1. Said protein triggers an HLA-A2-restricted immune response.

3 Claims, No Drawings

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Fragment of human protein encoded by the gene
      MUC-1

<400> SEQUENCE: 1

Ser Thr Ala Pro Pro Val His Asn Val
 1               5

<210> SEQ ID NO 2
<211> LENGTH: 9
<212> TYPE: PRT
<213> ORGANISM: Artificial Sequence
<220> FEATURE:
<223> OTHER INFORMATION: Fragment of human protein encoded by the gene
      MUC-1

<400> SEQUENCE: 2

Leu Leu Leu Leu Thr Val Leu Thr Val
 1               5
```

PEPTIDE FOR TRIGGERING AN IMMUNE REACTION AGAINST TUMOR CELLS

CROSS REFERENCE TO RELATED APPLICATIONS

This is a divisional application of U.S. Ser. No. 10/019,513 filed Aug. 6, 2002, issued as U.S. Pat. No. 7,087,712, issued Aug. 8, 2006, which is a U.S. National Stage application of International application No PCT/EP00/02699 filed Mar. 28, 2000 which claims priority from DE 19917195.5 filed Apr. 16, 1999.

BACKGROUND OF THE INVENTION

1. Field of the Invention

The present invention relates to a peptide that is derived from the MUC-1 gene, by which peptide a HLA-A2-restricted immune reaction against tumor cells can be triggered.

2. Description of Related Art

In an abstract to a lecture held on the 40. annual meeting of the American Society of Hematology, 1998, Brossart et al. show the possibility of deriving such a peptide from the MUC-1 gene, however, without mentioning the sequence of a peptide they tested or the localization of the sequence of a peptide that is not derived from the tandem repeat range of MUC-1.

Peptides for triggering an immune reaction against tumor cells are mentioned, for example, also in the publication by Finn, O. J., et al., (1995) "MUC-1 Epithelial Tumor Mucin-Based Immunity and Cancer Vaccines", Immunol Rev 145, pages 61-89, but without mentioning sequence information either.

By an immune reaction, for example the destruction of cells by such T cells that are also designated as cytotoxic T cells due to their ability to kill other cells is to be understood. In order to trigger such an immune reaction by cytotoxic T cells, foreign proteins e.g. as a result of a virus infection must be presented to the T cells by a MHC molecule on the cell surface.

These MHC molecules are peptide receptors which usually bind peptides within the cell in order to transport them to the cell surface, where the complex of peptide and MHC molecule can be recognized by T cells. In normal cells, the peptides bound by MHC molecules are derived from the usual cell-owned proteins. During their differentiation in an organism, T cells become tolerant against complexes of own peptides having own MHC molecules. Thus, each new peptide which comes up later, e.g. a peptide which is produced by a cell because of the infection with a virus, can be recognized by T cells.

There are two classes of MHC molecules, whereas those interacting with cytotoxic T cells belong to class I. Classic human class I molecules are HLA-A, B and C, wherein HLA-A2 represents a subclass of the HLA-A molecules.

If the accomplishment of an immune reaction is dependent on the existence of a certain MHC molecule, for example HLA-A2, this is said to be an MHC-restricted, e.g. a HLA-A2-restricted immune reaction. There are also sporadic T cell reactions which take place independently of MHC molecules. These are said to be MHC-unrestricted immune reactions.

In the publication by Finn et al. mentioned at the outset, for the treatment of a tumor patient it was suggested to trigger such a MHC-unrestricted immune reaction against a glycoprotein that is coded by the gene MUC-1 and exists on the surface of cells. The objective is herein to generate an effective immune response with a life-long immunity.

The protein coded by the gene MUC-1, which protein is also called MUC-1, is in most cases polarizedly expressed by normal epithelial cells such that it is normally not accessible for the immune system, like e.g. in the bowel, where it is expressed on the apical side of the epithelial cells, i.e. projecting into the bowel lumen.

However, MUC-1 is not polarizedly expressed on tumor cells, but covers all of the cell. The level of the expression is higher for tumor cells than for normal cells, but for tumor cells the molecules are not completely glycosylated, i.e. the side chains of saccharine molecules comprise a shortened structure with respect to MUC-1 that is produced by healthy cells. The incomplete glycosylation results in epitopes on the protein portion of MUC-1, which epitopes usually exist masked by saccharine side chains and are accessible on tumor cells for the immune system. Thus, the immune system can distinguish between this underglycosylated MUC-1 and the normal not underglycosylated MUC-1.

Beside the side chains made of saccharine molecules, another essential structure feature are the so-called tandem repeats. These are sequences of 20 amino acid residues which are each repeated in an identical or similar manner approximately 20 to 125 times in the MUC-1 molecule.

For triggering an effective immune reaction by T cells, co-stimulators are required, whereto do belong in particular the so-called dendritic cells which take up proteins presented from outside and can present them after their processing to peptides so that cytotoxic T cells can be activated thereby. Therefore, Finn et al. suggest to inject synthetic peptides which represent the MUC-1 tandem repeats, together with an adjuvans that attracts dendritic cells. An adjuvans is a substance which, when injected together with a substance against which an immune reaction is to be triggered, strengthens the response of the immune system to this substance in an unspecified manner. By such a vaccination, an MHC-unrestricted T cell reaction against the tandem repeats shall be obtained. It is even suggested to replace amino acids which can mediate a MHC-class-I-binding in the synthetic peptides by others so that no MHC-restricted T cells can arise by a presentation of the peptides by MHC class I molecules.

On the one hand, the problem of a possible autoimmunity can be reduced by avoiding an MHC-restricted immune response, on the other hand, the lower efficiency of an MHC-unrestricted immune response in comparison to an MHC-restricted one is a great disadvantage. Thus, the chances are also lower to make a tumor to disappear by means of an MHC-unrestricted immune response than by means of an MHC-restricted immune response.

For this reason, on the occasion of the presentation mentioned at the outset, the inventors of the present application have suggested to trigger a MHC-restricted immune response against MUC-1 expressing cells. They report that to this end the known MUC-1 amino acid sequence has been searched for HLA-A2 binding motives by means of a computer analysis. Peptides with a high binding probability were identified, synthesized and examined with respect to the regard whether they can induce cytotoxic T cells in vitro with the help of dendritic cells. The cytotoxic T cells created in that way developed an antigen-specific HLA-A2-restricted cytotoxic activity against these target cells that had been incubated before with the respective peptide by which the cytotoxic T cells were activated, or against MUC-1 expressing tumor cells.

SUMMARY OF THE INVENTION

In view of the above, it is an object of the present invention to provide at least one amino acid sequence for such a peptide for triggering an immune reaction against tumor cells.

This object is achieved according to the invention by the peptide comprising the sequence SEQ ID NO: 1 and/or a sequence that is derived from the signal peptide, in particular the sequence SEQ ID NO: 2 from the enclosed sequence listing, and/or a modified form of the sequence SEQ ID NO: 1 and/or of the sequence SEQ ID NO: 2.

The object underlying the invention is in that way completely achieved.

By means of the peptide according to the invention, cytotoxic T cells can be generated which develop an antigen-specific MHC-restricted cytotoxic activity against MUC-1 expressing tumor cells and which destroy the latter.

Thus, this peptide offers the possibility of an effective tumor therapy, in which the suppression of an immune reaction against tumor cells often observed in tumor patients can be reversed.

Peptide SEQ ID NO: 1 is a nonapeptide that is derived from the amino acid sequence of a tandem repeat of MUC-1 and that distinguishes from another peptide that has been described earlier, amongst others by two amino acids, the one of which allows a binding of the peptide to the HLA-A2 molecule.

DETAILED DESCRIPTION OF A PREFERRED EMBODIMENT

As can be seen from the embodiments, the inventors succeeded in proving that cytotoxic T cells killing in an MHC-class-I-restricted manner tumor cells that create MUC-1 could be created very effectively by means of the nonapeptide. Namely, these tumor cells present, via MHC class I molecules, certain fragments of all proteins generated by them. If now cytotoxic T cells recognize the peptide presented by a MHC class I molecule, by which peptide they were originally activated, they kill this cell. Thus, this peptide that is presented by MHC class I molecules of MUC-1 expressing cells offers the advantageous possibility to trigger selectively an immune reaction against tumors which generate MUC-1.

It was particularly surprising that even with the help of a peptide having a sequence that is not located in the mature MUC-1 protein on the cell surface, but only in the signal peptide of the immature protein, cytotoxic T cells can be induced which show an MHC-restricted cytotoxic activity against MUC-1 expressing tumor cells.

A signal peptide of the immature protein is understood to be a peptide that is coded by the gene MUC-1 and that is generated in the cell in one piece with the rest of the protein, but that is cleaved off from same in the course of the processing in the endoplasmatic reticulum of the cells.

Peptide SEQ ID NO: 2 is an example of a nonapeptide that is derived from the amino acid sequence of the signal peptide from MUC-1. This peptide results in an effective immune reaction against MUC-1 generating tumor cells. The possibility to create cytotoxic T cells which are directed against a further peptide presented by MHC-1 molecules has the advantage that the immune reaction against tumor cells can be even further increased by the simultaneous use of cytotoxic T cells which are directed against both peptides presented by MHC-1 molecules.

Moreover, via an MHC class I molecule, a signal peptide can be presented also from such MUC-1 producing tumor cells which, due to a degeneration, do not have a functioning system that trans-ports peptides created in the cytosol of the cell into the endoplasmatic reticulum (ER) which peptides are to be presented by MHC class I molecules. In the ER, namely, the peptides are first assembled with the MHC class I molecules and only then brought onto the cell surface. Since the signal peptide is cleaved off only in the ER, for its MHC-class-I-mediated presentation no transport into the ER is necessary. Thus, an immune reaction that was triggered by the peptide with the sequence SEQ ID NO: 2 can be directed against a larger number of tumor cells than an immune reaction that was triggered by peptides which are not derived from the MUC-1 signal peptide.

Modified forms of the peptides SEQ ID NO: 1 and/or 2 can also result in the desired immune response.

According to the invention, modified means each chemical, enzymatic or another modification of the peptide. This can be done e.g. already in the generation of the peptide or later by removing or adding individual amino acid residues, the exchange of individual amino acid residues, and also by the chemical modification of individual amino acid residues by adding certain chemical groups.

In another preferred embodiment, the invention relates to a nucleic acid which comprises a part of a sequence which codes for at least one peptide according to the invention. Furthermore, the nucleic acid may comprise further sequences which are necessary for the expression of the nucleic acid sequence corresponding to the peptide. The nucleic acid used can be contained in a vector which is suitable to allow the expression of the nucleic acid sequence corresponding to the peptide in a cell.

Such a nucleic acid has the advantage that it is chemically more stable and less sensitive than peptides. The handling, thus, is simpler than that of peptides, and the storability of nucleic acids is nearly indefinite. They can be produced cheaply by chemical and/or molecular-biological means and, in principle, can be produced in unlimited amounts. Nucleic acid sequences that may be necessary for the expression have the advantage, just like a vector that contains the nucleic acids, that it is thereby possible to produce large amounts of peptides in a very cost effective manner in cellular expression systems by means of nucleic acids. The nucleic acids can, however, also be used for transforming antigen-presenting cells, in particular dendritic cells, such that they generate the corresponding peptides themselves, and then presenting them to cytotoxic T cells or the precursor cells of same, respectively, by means of MHC-1 molecules.

Another aspect of the invention relates to a pharmaceutical composition which comprises a peptide according to the invention or a nucleic acid according to the invention, in an amount which is sufficient for triggering an MHC-1-restricted immune response.

To this end, the peptides and/or nucleic acids may be prepared in the common galenicals which are appropriate in each case. In the case of peptides, these can e.g. be preparations which are usually used for vaccinations and which contain an adjuvans. In the case of nucleic acids, also a preparation with liposomes or vesicles is possible. By means of an appropriate pharmaceutical preparation, it is possible to treat organisms directly, without having to withdraw antigen-presenting cells or the precursor cells of same, respectively, in order to culture these for a while and to bring them into the patient after having treated them with peptides or nucleic acids. By means of a suitable pharmaceutical preparation, a tumor treatment can be effected in the form of a vaccination.

Another aspect of the invention relates to the use of a nucleic acid according to the invention within the scope of a gene therapy.

Herein, the gene therapy can be performed by transformation of antigen-presenting cells, already described above, in particular of dendritic cells, which or the precursor cells of which were withdrawn from the body of an organism to be treated, prior to be brought again into the body after the transformation. In comparison to the use of peptides, the longer lasting presentation is advantageous herein, as explained above.

Another possibility is to bring the nucleic acid in the body such that it is selectively absorbed and expressed by antigen-presenting cells, in particular by dendritic cells. This application has the advantage that, apart from the administration, no further measures are necessary, like e.g. the culture and the selective reproduction of the withdrawn dendritic cells or the precursor cells of the same.

The invention further relates to the use of a nucleic acid according to the invention for the transformation or transfection of cells in vitro. The use of the nucleic acid in vitro has the advantage that processes, like e.g. the electroporation, and/or auxiliary materials, like e.g. calcium phosphate or DEAE dextran, can be used, which considerably facilitate and improve the absorption of nucleic acids into cells, but which are not applicable in vivo.

In this process, as already mentioned, antigen-presenting cells, in particular dendritic cells or the precursor cells thereof, respectively, can be treated, which were withdrawn from a patient and which later are brought again into the patient.

Another aspect of the present invention is the use of at least one peptide according to the invention or of one nucleic acid according to the invention for triggering an immune reaction in connection with a tumor therapy or a prophylactic treatment with respect to the development of a tumor. It is herein advantageous that the immune suppression and tolerance with respect to MUC-1 often observed in tumor diseases can be reversed by the peptides' or nucleic acids' use according to the invention.

A prophylactic treatment is in particular advantageous for persons who have a high risk of developing a tumor, e.g. caused by hereditary or because they already had a tumor in earlier times.

In an improvement, the application of peptides or nucleic acids according to the invention is performed in combination with a Pan-HLA-DR-binding peptide.

In the use of such a Pan-HLA-DR-binding peptide it is advantageous that the antigen-specific cytotoxic activity of the generated T cells is reinforced.

In an improvement, at least one of the peptides or one of the nucleic acids according to the invention is incubated together with antigen-presenting cells, in particular with dendritic cells, and only then is brought into an organism from which the antigen-presenting cells or the precursor cells of the same were withdrawn before.

The advantage of this process is that when triggering an immune reaction in this way the success is safer and more controllable than with the injection of a peptide together with an adjuvans, for which the immune reaction may happen stronger or weaker. Just for a tumor therapy, however, success for triggering an immune reaction should be made sure, so that no precious time gets lost because of an ineffective treatment.

It is to be understood that the features mentioned above and those yet to be explained below can be used not only in the respective combinations indicated, but also in other combinations or in isolation, without leaving the scope of the present invention.

Embodiments of the invention will be shown and explained in the description below.

Example 1

Induction of Antigen-Specific Cytotoxic T Cells by Using Peptides and Dendritic Cells 1.1 Providing Dendritic Cells As e.g. described by Brossart, P., et al., Cancer Res 58 (1998), pages 732 ff.; first of all, mononuclear cells of peripheral blood were isolated from buffy coat preparations of heparinized blood of three healthy donators by Ficoll/Paque (Gibco-BRL, Grand Island, N.Y.) density-gradient centrifugation. The cells were seeded in cell culture bowls in RP10 medium. After two hours at 37° C., the cells that did not adhere were removed and the adhering blood monocytes were cultivated in RP10 medium that contained the following cytokine additives: human recombinant GM-CSF (Leukomax, Sandoz, 100 ng/ml), IL-4 (Genzyme, 1000 IU/ml), and TNF-α (Genzyme, 10 ng/ml). After seven days of cultivation, in the FACS analysis the cells showed a strong expression of the surface marker MHC class I and II, CD83, CD80, CD86, CD40 and CD54, characteristic of the phenotype of mature dendritic cells, and therefore were identified as dendritic cells.

1.2 Identification of Suitable Peptides

For identifying peptides which were presented by HLA-A2 with a high probability, first of all, the amino acid sequence coded by the gene MUC-1 was searched for potential HLA-A*0201 (a certain HLA-A2 type) binding peptide motives by means of a computer program, as described, for example, in Rammensee, H. G., et al., Landes Bioscience, Austin, Tex., USA (1997).

The selected sequences and control sequences as well as a PAN-HLA-DR-binding peptide were synthesized on a peptide synthesizer by using standard Fmoc chemistry.

1.3 Induction of Cytotoxic T Cells $5 \times 10^5$ dendritic cells from 1.1 were incubated with 50 µg/ml synthetic peptide from 1.2 for two hours, washed, and incubated with $2.5 \times 10^6$ autologous, i.e. coming from the same donators, mononuclear cells of periphery blood in RP10 medium. Additionally to the control peptides and the potentially HLA-A2 binding peptides the dendritic cells were partly incubated with 50 µg/ml of a PAN-HLA-DR-binding peptide which represents a T helper epitope.

After seven days of cultivation, the cells were again stimulated by adding autologous, mononuclear cells of peripheral blood pre-incubated with the synthetic peptide from 1.2. On the first, third and fifth day, respectively, 1 ng/ml human recombinant IL-2 (Genzyme) was added. The cytokine IL-2 is necessary for the cultivation and reproduction of cytotoxic T cells. Altogether, stimulation was effected up to three times in an interval of a week.

1.4 Proof of Cytotoxic T Cell Activity

T2 cells which are distinguished by the fact that they can generate HLA-A2, but cannot present peptides synthesized by themselves via this MHC class I molecules, were pre-incubated with 50 µg/ml of synthetic peptide from 1.2 for two hours and marked with [$^{51}$Cr]-sodium chromate in RP10 at 37° C. for one hour. In each case $10^4$ of these cells were transferred into each of a well of a 96-well-plate. Cytotoxic T cells that were generated before according to 1.3 were added, so that, respectively, an end volume of 200 µl per well was reached. Subsequently, incubation took place for four hours at 37° C. If now the cytotoxic T cells kill the cells that were labeled with $^{51}$Cr before, they lyse these cells, and the $^{51}$Cr contained in the cells is released. At the end of the experiment in the cell supernatants taken off, the released radioactivity is determined by counting in a β-counter. In that way, a measure for the cytotoxic activity of T cells is obtained.

1.5 Peptides Triggering a HLA-A2-Restricted Immune Response

Two of the synthesized peptides which are derived from the sequence of the MUC-1 gene were able to induce cytotoxic T cells in vitro by means of dendritic cells in the process mentioned above. These are the two peptides with the sequence SEQ ID NO: 1 and the sequence SEQ ID NO: 2 from the sequence protocol. The cytotoxic T cells that were induced by using the peptide with the sequence SEQ ID NO: 1 were able to specifically kill T2 cells that were pre-treated with exactly this peptide, whereas they were not able to kill T2 cells that were pre-treated with other peptides. On the other hand, cytotoxic T cells which were induced by using other peptides were not able to kill T2 cells which were pre-treated with the peptide with the sequence SEQ ID NO: 1. Cytotoxic T cells which were induced by using the peptide with the sequence SEQ ID NO: 2 do behave in the same way. These cells could kill only those cells which were pre-treated with the peptide with the sequence SEQ ID NO: 2.

In this process, cytotoxic T cells which were induced in the presence of the PAN-HLA-DR-binding peptide showed a higher cytotoxic activity than those which were induced when this peptide was not present.

Example 2

Lysis of Tumor Cells by MUC-1 Peptide Specific Cytotoxic T Cells

Different tumor cell lines that express either both HLA-A2 and MUC-1 or only one of the two cell surface molecules, respectively, as proven by FACS-analysis, were labeled with $^{51}$Cr, as described under 1.4 for T cells. After that, as also described under 1.4, the cells were incubated with cytotoxic T cells which were induced as described under 1.3.

Those T cells that were activated by using the peptides with the sequence SEQ ID NO: 1 or the sequence SEQ ID NO: 2 were able to lyse tumor cells of the lines MCF-7 (breast cancer cells), A-498 (kidney cell carcinoma cells) and MZ1774-RCC (kidney cell carcinoma cells) which express HLA-A2 and MUC-1. However, they were not able to lyse cells of the cell lines Croft (EBV immortalized B cells) which do not express MUC-1, as well as Caki-2 (kidney cell carcinoma cells), SK-OV-3 (ovary cancer cells) and K562 (pro-erythroblastic cells) which do not express HLA-A2.

The cytotoxic T cells that were activated by using the peptides with the sequence SEQ ID NO: 1 and SEQ ID NO: 2 could neither lyse the kidney cell carcinoma cells of the line MZ1774-RCC expressing HLA-A2 and MUC-1, if the kidney cell carcinoma cells were incubated before with 10 μg/ml of a monoclonal antibody (BB7.2, Coulter-Immunotech) directed against HLA-A2 for 30 minutes.

These results show that the cytotoxic T cells generated by using the peptides according to the invention kill only tumor cells which express both HLA-A2 and MUC-1.

Thus, the peptides according to the invention are suitable for triggering an immune reaction against certain tumor cells also within the scope of a therapy.

First studies in which such a therapy was used for patients suffering from breast cancer and in which the patients have responded to the immune therapy will soon be finished.

What is claimed is:

1. An isolated HLA-A2 binding peptide having an amino acid sequence from a signal peptide encoded by the MUC-1 gene, wherein the peptide produces an immune reaction against MUC-1 expressing tumor cells wherein said peptide consists of SEQ ID NO:2: Leu Leu Leu Leu Thr Val Leu Thr Val.

2. A pharmaceutical composition comprising the peptide of claim 1.

3. A method for tumor therapy of tumors expressing MUC-1, comprising the steps of: incubating the peptide of claim 1 together with dendritic cells from a patient having a MUC-1 expressing tumor; and administering the incubated cells to said patient.

* * * * *